United States Patent
Tao et al.

(10) Patent No.: US 8,045,771 B2
(45) Date of Patent: Oct. 25, 2011

(54) SYSTEM AND METHOD FOR AUTOMATED PATIENT ANATOMY LOCALIZATION

(75) Inventors: Xiaodong Tao, Niskayuna, NY (US);
James Vradenburg Miller, Clifton Park, NY (US); Mukta Chandrashekhar Joshi, Belmont, MA (US); Robert Franklin Senzig, Germantown, WI (US)

(73) Assignee: General Electric Company, Niskayuna, NY (US)

( * ) Notice: Subject to any disclaimer, the term of this patent is extended or adjusted under 35 U.S.C. 154(b) by 985 days.

(21) Appl. No.: 11/986,494

(22) Filed: Nov. 21, 2007

(65) Prior Publication Data
US 2008/0159611 A1  Jul. 3, 2008

Related U.S. Application Data

(60) Provisional application No. 60/860,639, filed on Nov. 22, 2006.

(51) Int. Cl.
*G06K 9/00* (2006.01)
(52) U.S. Cl. ........ 382/128; 382/131; 382/132; 382/293; 382/294; 378/8
(58) Field of Classification Search .............. 382/128, 382/131, 132, 154, 294
See application file for complete search history.

(56) References Cited

U.S. PATENT DOCUMENTS

| | | | |
|---|---|---|---|
| 6,826,423 B1 * | 11/2004 | Hardy et al. | 600/429 |
| 6,922,457 B2 * | 7/2005 | Nagata et al. | 378/19 |
| 7,245,691 B2 * | 7/2007 | Kiyono | 378/4 |
| 7,684,604 B2 * | 3/2010 | Bystrov et al. | 382/131 |
| 7,747,308 B2 | 6/2010 | Hundley et al. | |
| 2004/0030246 A1 * | 2/2004 | Townsend et al. | 600/427 |
| 2005/0010445 A1 * | 1/2005 | Krishnan et al. | 705/2 |
| 2007/0081706 A1 * | 4/2007 | Zhou et al. | 382/128 |
| 2009/0161937 A1 | 6/2009 | Peng et al. | |
| 2010/0061632 A1 | 3/2010 | Young et al. | |
| 2010/0129005 A1 | 5/2010 | Tao et al. | |

* cited by examiner

*Primary Examiner* — Tom Y Lu
(74) *Attorney, Agent, or Firm* — Jason K. Klindtworth

(57) ABSTRACT

A method of imaging comprises performing a scout image of an object and aligning major regions of interest within the object by comparing the scout image with a pre-determined atlas image. In a further embodiment, a method of imaging using a computed tomography (CT) scanner is provided and comprises performing a scout image of a subject and aligning major anatomical regions of interest within the subject by comparing the scout image with a pre-determined atlas image. Further, an imaging system for us with a computed tomography (CT) imaging device is provided and comprises a processor configured to perform aligning major anatomical regions of interest within a subject by comparing a scout image with a pre-determined atlas image, and wherein the major anatomical regions are used for automated localization for Scan Range and/or Exam split.

14 Claims, 2 Drawing Sheets

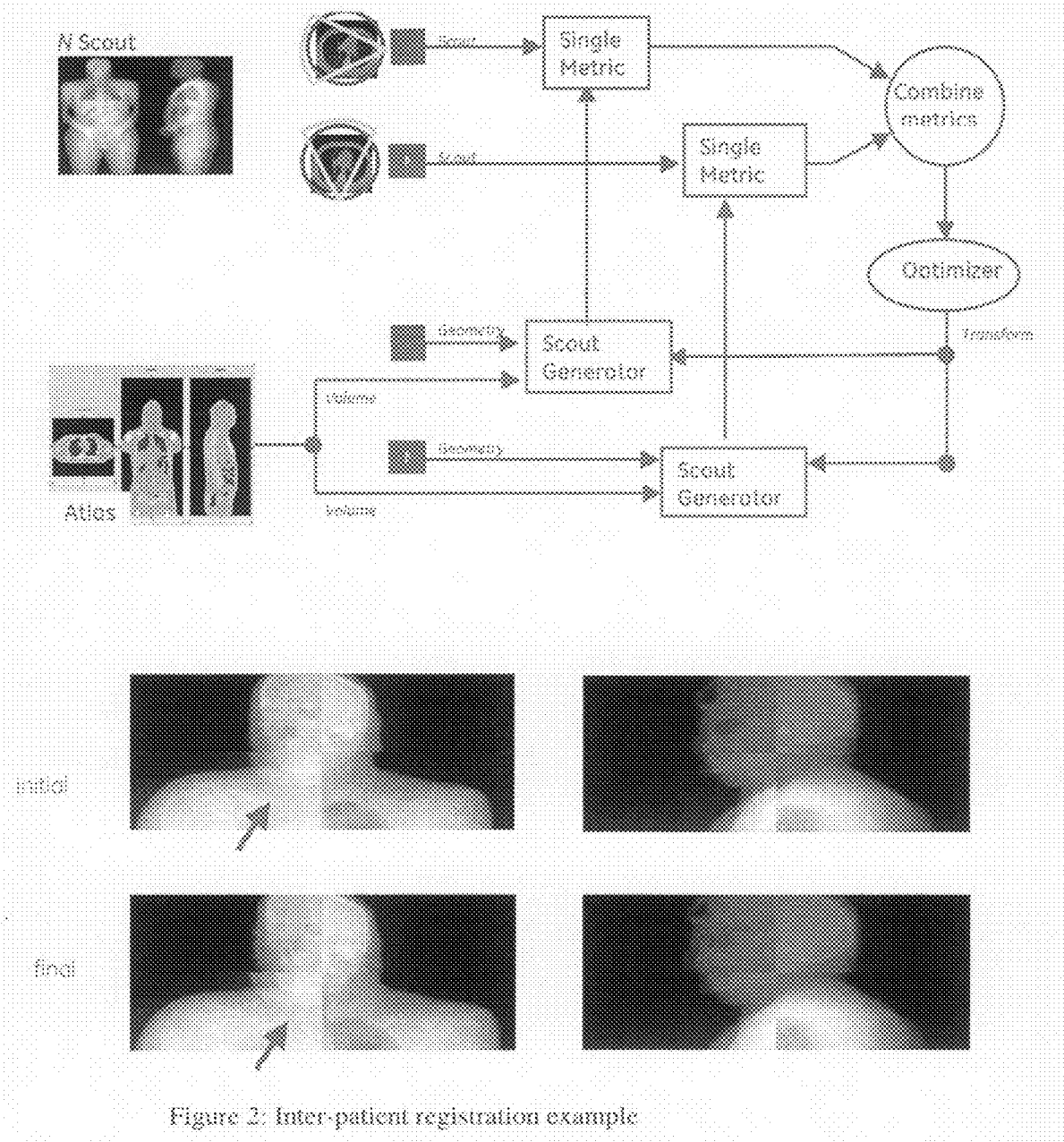

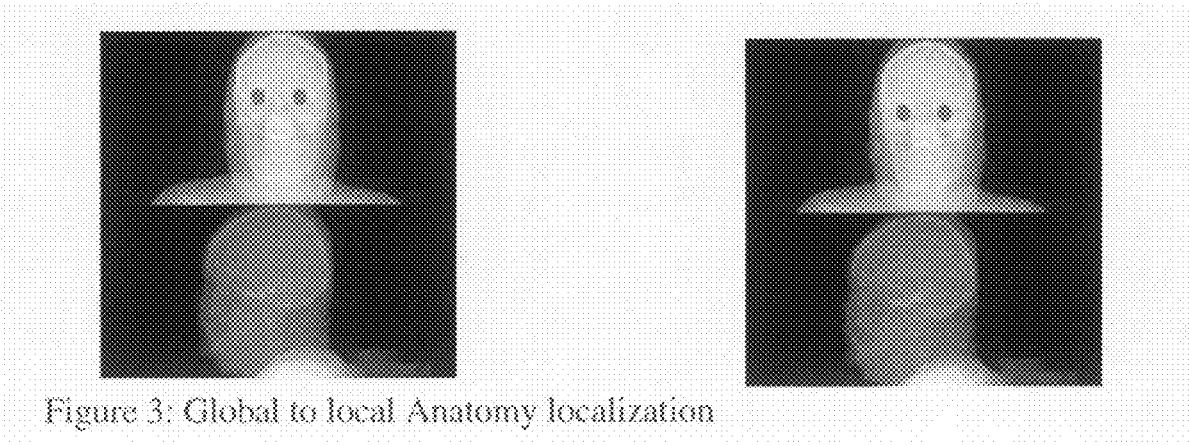
Figure 3: Global to local Anatomy localization

SYSTEM AND METHOD FOR AUTOMATED PATIENT ANATOMY LOCALIZATION

CROSS REFERENCE TO RELATED APPLICATIONS

This application is related to Provisional Application U.S. Ser. No. 60/860,639, entitled "SYSTEM AND METHOD FOR AUTOMATED PATIENT ANATOMY LOCALIZATION USING SCOUTS", filed Nov. 22, 2006, the contents of which are herein incorporated by reference and the benefit of priority to which is claimed under 35 U.S.C. 119(e).

BACKGROUND

In the current computed tomography (CT) image acquisition process, X-Ray scout images are acquired for anatomy localization. An operator reviews the scouts and sets scanning parameters to acquire images of patient region of interest. Patient anatomy is unknown to the scanner. Furthermore, after the images have been reconstructed, typically the operator has to divide the scanned images into anatomical regions to bill and network to the appropriate department within radiology e.g. Chest, Abdomen etc. This is called Exam Split.

The annotation on the images depends on the patient's orientation within the gantry at the time of scanning. This orientation (whether head first or feet first etc) is manually entered by the operator. There have been times when this orientation is either entered incorrectly or due to other factors, the patient orientation was changed after the orientation on the scanner prescription was entered. This causes the annotation of the patient images to be incorrect which can lead to serious consequences.

There is a need for an automated process of Exam Split. Further there is a need for the scanner to be able to identify anatomy, and therefore it can also identify the orientation of the patient when scanning and the annotation of the images will be directly correlated to the actual scanned data, thus eliminating errors as described above.

BRIEF DESCRIPTION

In a first aspect, a method of imaging comprises performing a scout image of an object and aligning major regions of interest within the object by comparing the scout image with a pre-determined atlas image.

In a second aspect, a method of imaging using a computed tomography (CT) scanner is provided and comprises performing a scout image of a subject and aligning major anatomical regions of interest within the subject by comparing the scout image with a pre-determined atlas image.

In a third aspect, an imaging system for us with a computed tomography (CT) imaging device is provided and comprises a processor configured to perform aligning major anatomical regions of interest within a subject by comparing a scout image with a pre-determined atlas image, and wherein the major anatomical regions are used for automated localization for Scan Range and/or Exam split.

DRAWINGS

These and other features, aspects, and advantages of the present invention will become better understood when the following detailed description is read with reference to the accompanying drawings in which like characters represent like parts throughout the drawings, wherein:

FIG. 1 is a schematic illustration of a registration framework to which embodiments of the present invention are applicable;

FIG. 2 is an exemplary illustration of images obtained using methods of the present invention; and, FIG. 3 is an exemplary illustration of images obtained using methods of the present invention.

DETAILED DESCRIPTION

This invention solves the problem of automatic localization of patient anatomy. This can be done from one or more scout images or from a 3D dataset acquired from a low dose helical "scout". For example, in a typical CT imaging session, two scout images are acquired first. An operator reviews the scouts and sets scanning parameters to acquire images of patient region of interest. This invention automates this process by automatically finding the patient anatomy from the scout image(s) (2D or 3D). This also allows for automation of the Exam Split process thus improving the workflow and increasing the efficiency.

In embodiments of the present invention, there is provided a system and method to automatically localize patient anatomy from scout images (one or more 2D scouts or a low dose helical scout) by registering a pre-labeled atlas into the patient space and transforming the atlas labels to find patient anatomy. The system can also recognize the patient orientation. The system can be used in medical imaging devices for automatic image range prescription, more accurate patient-centric dose management, automatic exam split, as well as for correct identification of patient orientation and for automated reconstruction parameter optimization per anatomy.

Modern medical imaging devices can acquire patient images with better quality in shorter time. What they see, however, is nothing more than a collection of numbers. The accurate patient anatomy is completely unknown to the scanner. Therefore, an operator's involvement is often required to figure out the patient position and orientation from a number of scout images and to set scanning parameters appropriate for the study to be conducted. Moreover, since the patient anatomy is unknown to the medical imaging devices, dose management can only be implemented in a device centric way.

In order to tackle the problem of anatomy localization from scouts, a framework for registering a 3D volumetric atlas to one or more scout images is provided. The resulting transformation is then used to transform the atlas segmentation (anatomical labels) to the patient space to localize patient anatomy.

Referring to FIG. 1, architecture for this registration framework is shown. In the step of aligning atlas to the scout images, simulated scout images of a spatially transformed version of the atlas are generated with the same scanner geometry. The simulated images are compared with the patient scout images for a similarity measurement, which is then used to update the transform to improve the alignment between the atlas and the patient.

To get an accurate estimation of the position/orientation of patient organ/region of interest, a global to local search strategy is employed that aligns major body sections first, and switches to local regions to localize detailed patient anatomy. In one embodiment one could use the Single metric as Mutual Information, the Many-to-One metric as a weighted sum of the single metrics, the optimizer could be one does not require gradient information e.g. Amoebae style optimizer. Those skilled in the art would recognize that a variety of metric could be used to measure the similarity as well as a variety of optimization techniques could be used to estimate the parameters of the transformation. The Scout generator uses the scanner geometry and the current estimation of the transformation to generate the hypothesized Atlas Scout Image. See example result in FIG. 2. Referring now to the FIG. 3 shows the transfer of the labels from the atlas to the target. Initially without registration the label was in the wrong location, after the registration, the label is seen to be in the correct location on the target.

In a first embodiment, a method of imaging comprises performing a scout image of an object and aligning major regions of interest within the object by comparing the scout image with a pre-determined atlas image. The aligning step further comprises calculating a similarity measurement between the scout image and atlas image. Further, the method comprises identifying more detailed or finer regions of interest contained within the object after aligning the major regions of interest to localize detailed regions of interest.

In embodiments of the present invention, the object is a patient and the major regions of interest comprise anatomical regions of interest comprising chest, abdomen, pelvis, and combinations thereof. The detailed or finer regions of interest comprise organs and anatomical structures comprising eyes, breasts, liver, and combinations thereof. The scout and atlas images are acquired with a same computed tomography (CT) scanner geometry. In a further embodiment, the scout and atlas images are acquired with one of multiple two-dimensional (2D) scouts or a low dose helical acquisition.

In another embodiment, a method of imaging using a computed tomography (CT) scanner comprises performing a scout image of a subject and aligning major anatomical regions of interest within the subject by comparing the scout image with a pre-determined atlas image. The anatomical regions are used for automated localization for Scan Range and/or Exam split. Further, the anatomical regions are used for automatic identification of patient orientation within a gantry of the CT scanner. In a further embodiment, the method comprises using information corresponding to the major anatomical regions of interest for automated post processing steps comprising anatomy based reformat, anatomy based context sensitive processing to extract relevant information, Computer Aided detection of pathology and combinations thereof.

In a further embodiment, an imaging system for us with a computed tomography (CT) imaging device is provided and comprises a processor configured to perform aligning major anatomical regions of interest within a subject by comparing a scout image with a pre-determined atlas image, and wherein the major anatomical regions are used for automated localization for Scan Range and/or Exam split. Further, the anatomical regions are used for automatic identification of patient orientation within a gantry of the CT imaging device. In a further embodiment, the processor is further configured for using information corresponding to the major anatomical regions of interest for automated post processing steps comprising anatomy based reformat, anatomy based context sensitive processing to extract relevant information, Computer Aided detection of pathology and combinations thereof.

It is to be appreciated that there are a number of applications and uses for the present invention, for example:

The method of identifying gross body parts or organ locations by mapping information to pre-scan imagery in the form of multiple 2D scouts or a low dose helical acquisition.

The method of identifying gross body parts or organ locations by mapping information from an anatomical atlas to pre-scan imagery in the form of multiple 2D scouts or a low dose helical acquisition.

Automatic identification of gross body areas e.g. Chest, abdomen, pelvis etc.

Automatic identification of more detailed organs and structures e.g. eyes, breasts, liver etc Use of anatomy information for dose management to individual structures Use of anatomy information for automated localization for Scan Range, Exam split Use of anatomy information for automated post processing steps including but not limited to anatomy based reformat, anatomy based context sensitive processing to extract relevant information, Computer Aided detection of pathology Automatic optimization of reconstruction parameters per anatomy e.g. recon kernels, display field of view which affects resolution, image thickness etc.

Use of anatomy information for automatic identification of patient orientation within the Scanner gantry. This can ensure correct annotation of the images without relying on operator input and reducing errors caused by incorrect input.

Use of Anatomy information to automatically assign correct preset for Window & Level, which can be used in a pure CT as well as a PET/CT system.

This has broad applications through out the system from acquisition protocol to post processing and in overall workflow through automation of different steps.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed:

1. A method of imaging comprising:
performing a scout image of an object;
aligning major regions of interest within the object by comparing the scout image with a pre-determined atlas image to define a limited scan range for image acquisition;
acquiring image data based on the limited scan range.

2. The method of claim 1 wherein the aligning step further comprises calculating a similarity measurement between the scout image and altas image.

3. The method of claim 1 further comprising identifying more detailed or finer regions of interest contained within the object after aligning the major regions of interest to localize detailed regions of interest.

4. The method of claim 1 wherein the object is a patient and the major regions of interest comprise anatomical regions of interest comprising chest, abdomen, pelvis, and combinations thereof.

5. The method of claim 3 wherein the detailed or finer regions of interest comprise organs and anatomical structures comprising eyes, breasts, liver, and combinations thereof.

6. The method of claim 1 wherein the scout and atlas images are acquired with a same computed tomography (CT) scanner geometry.

7. The method of claim 6 wherein the scout and atlas images are acquired with one of multiple two-dimensional (2D) scouts or a low dose helical acquisition.

8. A method of imaging using a computed tomography (CT) scanner comprising:
performing a scout image of a subject;

aligning major anatomical regions of interest within the subject by comparing the scout image with a pre-determined atlas image to define a limited scan range for image acquisition;

acquiring image data based on the limited scan range.

9. The method of claim 8 further comprising identifying more detailed or finer regions of interest contained within the subject after aligning the major anatomical regions of interest to localize detailed regions of interest.

10. The method of claim 9 wherein the major anatomical regions of interest comprise chest, abdomen, pelvis, and combinations thereof.

11. The method of claim 9 wherein the detailed or finer regions of interest comprise organs and anatomical structures comprising eyes, breasts, liver, and combinations thereof.

12. The method of claim 8 wherein the major anatomical regions are used for automated localization for Exam split.

13. The method of claim 8 wherein the anatomical regions are used for automatic identification of patient orientation within a gantry of the CT scanner.

14. The method of claim 8 further comprising:

using information corresponding to the major anatomical regions of interest for automated post processing steps comprising anatomy based reformat, anatomy based context sensitive processing to extract relevant information, Computer Aided detection of pathology and combinations thereof.

* * * * *

UNITED STATES PATENT AND TRADEMARK OFFICE
CERTIFICATE OF CORRECTION

PATENT NO. : 8,045,771 B2  Page 1 of 1
APPLICATION NO. : 11/986494
DATED : October 25, 2011
INVENTOR(S) : Tao et al.

It is certified that error appears in the above-identified patent and that said Letters Patent is hereby corrected as shown below:

In Column 4, Line 47, in Claim 2, delete "altas" and insert -- atlas --, therefor.

Signed and Sealed this
Ninth Day of October, 2012

David J. Kappos
*Director of the United States Patent and Trademark Office*